US010995371B2

(12) United States Patent
Hogan et al.

(10) Patent No.: US 10,995,371 B2
(45) Date of Patent: May 4, 2021

(54) COMPOSITION AND METHOD OF DNA MARKING ELASTOMERIC MATERIAL

(71) Applicant: APDN (B.V.I.) Inc., Tortola (VG)

(72) Inventors: Michael Hogan, Stony Brook, NY (US); In-Young Yang, East Setauket, NY (US); Yuhua Sun, Stony Brook, NY (US); Lawrence Jung, Dix Hills, NY (US)

(73) Assignee: APDN (B.V.I.) Inc., Stony Brook, NY (US)

( * ) Notice: Subject to any disclaimer, the term of this patent is extended or adjusted under 35 U.S.C. 154(b) by 360 days.

(21) Appl. No.: 15/722,157

(22) Filed: Oct. 2, 2017

(65) Prior Publication Data

US 2018/0105873 A1   Apr. 19, 2018

Related U.S. Application Data

(60) Provisional application No. 62/407,819, filed on Oct. 13, 2016.

(51) Int. Cl.
*C12Q 1/68* (2018.01)
*C12Q 1/6869* (2018.01)
*C12Q 1/6874* (2018.01)
*C22C 21/14* (2006.01)

(52) U.S. Cl.
CPC ............. *C12Q 1/6869* (2013.01); *C12Q 1/68* (2013.01); *C12Q 1/6874* (2013.01); *C22C 21/14* (2013.01)

(58) Field of Classification Search
CPC .................................................. C12Q 1/6869
See application file for complete search history.

(56) References Cited

U.S. PATENT DOCUMENTS

| | | |
|---|---|---|
| 4,183,989 A | 1/1980 | Tooth |
| 4,278,557 A | 7/1981 | Elwell, Jr. |
| 4,454,171 A | 6/1984 | Diggle, Jr. et al. |
| 4,548,955 A | 10/1985 | Okahata et al. |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,861,620 A | 8/1989 | Azuma et al. |
| 4,965,188 A | 10/1990 | Mullis et al. |
| 5,047,519 A | 9/1991 | Hobbs, Jr. et al. |
| 5,075,216 A | 12/1991 | Innis et al. |
| 5,089,691 A | 2/1992 | Morisaki et al. |
| 5,132,242 A | 7/1992 | Cheung |
| 5,139,812 A | 8/1992 | Lebacq |
| 5,151,507 A | 9/1992 | Hobbs, Jr. et al. |
| 5,156,765 A | 10/1992 | Smrt et al. |
| 5,176,203 A | 1/1993 | Larzul |
| 5,270,183 A | 12/1993 | Corbett et al. |
| 5,415,839 A | 5/1995 | Zaun et al. |
| 5,429,952 A | 7/1995 | Garner et al. |
| 5,451,505 A | 9/1995 | Dollinger |
| 5,498,283 A | 3/1996 | Botros et al. |
| 5,508,197 A | 4/1996 | Hansen et al. |
| 5,595,871 A | 1/1997 | DelVecchio et al. |
| 5,599,578 A | 2/1997 | Butland |
| 5,602,381 A | 2/1997 | Hoshino et al. |
| 5,639,603 A | 6/1997 | Dower et al. |
| 5,643,728 A | 7/1997 | Slater et al. |
| 5,736,314 A | 4/1998 | Hayes et al. |
| 5,763,176 A | 6/1998 | Slater et al. |
| 5,776,713 A | 7/1998 | Garner et al. |
| 5,849,208 A | 12/1998 | Hayes et al. |
| 5,866,336 A | 2/1999 | Nazarenko et al. |
| 5,912,257 A | 6/1999 | Prasad et al. |
| 5,942,444 A | 8/1999 | Rittenburg et al. |
| 5,956,172 A | 9/1999 | Downing |
| 5,977,436 A | 11/1999 | Thomas et al. |
| 5,989,823 A | 11/1999 | Jayasena et al. |
| 6,013,789 A | 1/2000 | Rampal |
| 6,030,657 A | 2/2000 | Butland et al. |
| 6,033,880 A | 3/2000 | Haff et al. |
| 6,057,370 A | 5/2000 | Weiland et al. |
| 6,127,120 A | 10/2000 | Graham et al. |
| 6,132,996 A | 10/2000 | Hunicke-Smith |
| 6,140,075 A | 10/2000 | Russell et al. |
| 6,169,174 B1 | 1/2001 | Hasegawa et al. |
| 6,261,809 B1 | 7/2001 | Bertling et al. |
| 6,287,768 B1 | 9/2001 | Chenchik et al. |
| 6,312,911 B1 | 11/2001 | Bancroft et al. |

(Continued)

FOREIGN PATENT DOCUMENTS

| | | | |
|---|---|---|---|
| CN | 103354001 | * | 3/2016 |
| EP | 0623658 A2 | | 11/1994 |

(Continued)

OTHER PUBLICATIONS

Annex 5, WHO good Distribution Practices for Pharmaceutical Products, WHO Technical Report Series, No. 957, pp. 235-264 (2010).
Notice of Reasons for Rejection issued in Japanese Patent Application No. JP2016-562831 dated Jul. 3, 2017.
Kim, Jeong AH et al., "Fabrication and Characterization of a PDMS-Glass Hybrid Continuous-Flow PCR Chip", Biochemical Engineering Journal, 29, 91-97 (2006).
Curcio, Mario et al., "Continuous Segmented-Flow Poymerase Chain Reaction for High-Throughput Miniaturized DNA Amplification" Analytical Chemistry, vol. 75, No. 1, 1-7 ( Jan. 1, 2003).
Kopp, Martin U. et al, "Chemical Amplification: Continuous-Flow PCR on a Chip", Science, vol. 280, 1046-1048 (1998).

(Continued)

*Primary Examiner* — Jezia Riley
(74) *Attorney, Agent, or Firm* — Clay D. Shorrock; Lowndes

(57) ABSTRACT

Methods of incorporating coded DNA into elastomeric materials and compositions thereof are claimed. Methods of recovering information from elastomeric materials with coded DNA and authenticating silicone objects with coded DNA are also claimed.

7 Claims, No Drawings

(56) References Cited

U.S. PATENT DOCUMENTS

| | | |
|---|---|---|
| 6,326,489 B1 | 12/2001 | Church et al. |
| 6,342,359 B1 | 1/2002 | Lee et al. |
| 6,361,944 B1 | 3/2002 | Mirkin et al. |
| 6,379,897 B1 | 4/2002 | Weidenhammer et al. |
| 6,399,397 B1 | 6/2002 | Zarling et al. |
| 6,537,747 B1 | 3/2003 | Mills, Jr. et al. |
| 6,537,752 B1 | 3/2003 | Astle |
| 6,576,422 B1 | 6/2003 | Weinstein et al. |
| 6,608,228 B1 | 8/2003 | Cumpston et al. |
| 6,613,560 B1 | 9/2003 | Tso et al. |
| 6,632,653 B1 | 10/2003 | Astle |
| 6,686,149 B1 | 2/2004 | Sanchis et al. |
| 6,703,228 B1 | 3/2004 | Landers et al. |
| 6,709,692 B2 | 3/2004 | Sudor |
| 6,743,640 B2 | 6/2004 | Whitten et al. |
| 6,995,256 B1 | 2/2006 | Li et al. |
| 7,014,113 B1 | 3/2006 | Powell et al. |
| 7,015,030 B1 | 3/2006 | Fouillet et al. |
| 7,031,927 B1 | 4/2006 | Beck et al. |
| 7,060,874 B2 | 6/2006 | Wilkins |
| 7,112,616 B2 | 9/2006 | Takizawa et al. |
| 7,115,301 B2 | 10/2006 | Sheu et al. |
| 7,133,726 B1 | 11/2006 | Atwood et al. |
| 7,160,996 B1 | 1/2007 | Cook |
| 7,223,906 B2 | 5/2007 | Davis |
| 7,250,195 B1 | 7/2007 | Storey et al. |
| 7,709,250 B2 | 5/2010 | Corbett et al. |
| 7,732,492 B2 | 6/2010 | Makino et al. |
| 8,278,807 B2 | 10/2012 | Agneray et al. |
| 8,597,549 B2 | 12/2013 | Cumpston et al. |
| 9,266,370 B2 | 2/2016 | Jung et al. |
| 9,297,032 B2 | 3/2016 | Jung et al. |
| 2001/0039018 A1 | 11/2001 | Matson et al. |
| 2002/0048822 A1 | 4/2002 | Rittenburg et al. |
| 2002/0051969 A1 | 5/2002 | Goto et al. |
| 2002/0056147 A1 | 5/2002 | Dau et al. |
| 2002/0064639 A1 | 5/2002 | Rearick et al. |
| 2002/0080994 A1 | 6/2002 | Lofgren et al. |
| 2002/0119485 A1 | 8/2002 | Morgan |
| 2002/0128234 A1 | 9/2002 | Hubbell et al. |
| 2002/0129251 A1 | 9/2002 | Itakura et al. |
| 2002/0137893 A1 | 9/2002 | Burton et al. |
| 2002/0155490 A1 | 10/2002 | Skinner et al. |
| 2002/0160360 A1 | 10/2002 | Chenchik et al. |
| 2002/0167161 A1 | 11/2002 | Butland |
| 2002/0185634 A1 | 12/2002 | Marder et al. |
| 2002/0187263 A1 | 12/2002 | Sheu et al. |
| 2003/0000225 A1 | 1/2003 | Nagai et al. |
| 2003/0017551 A1 | 1/2003 | Parthasarathy et al. |
| 2003/0031340 A1 | 2/2003 | Alattar et al. |
| 2003/0035917 A1 | 2/2003 | Hyman |
| 2003/0064507 A1 | 4/2003 | Gallagher et al. |
| 2003/0096273 A1 | 5/2003 | Gagna |
| 2003/0142704 A1 | 7/2003 | Lawandy |
| 2003/0142713 A1 | 7/2003 | Lawandy |
| 2003/0162296 A1 | 8/2003 | Lawandy |
| 2003/0177095 A1 | 9/2003 | Zorab et al. |
| 2003/0203387 A1 | 10/2003 | Pelletier |
| 2003/0207331 A1 | 11/2003 | Wilson, Jr. et al. |
| 2004/0063117 A1 | 4/2004 | Rancien et al. |
| 2004/0071718 A1 | 4/2004 | Tsai |
| 2004/0115796 A1 | 6/2004 | Burns |
| 2004/0166520 A1 | 8/2004 | Connolly |
| 2004/0219287 A1 | 11/2004 | Regan et al. |
| 2005/0008762 A1 | 1/2005 | Sheu et al. |
| 2005/0031120 A1 | 2/2005 | Samid |
| 2005/0045063 A1 | 3/2005 | Niggemann et al. |
| 2005/0053968 A1 | 3/2005 | Bharadwaj et al. |
| 2005/0059029 A1 | 3/2005 | Mariella, Jr. et al. |
| 2005/0059059 A1 | 3/2005 | Liang |
| 2005/0089970 A1 | 4/2005 | Bradburne et al. |
| 2005/0112610 A1 | 5/2005 | Lee et al. |
| 2005/0142565 A1 | 6/2005 | Samper et al. |
| 2005/0214532 A1 | 9/2005 | Kosak et al. |
| 2005/0260609 A1 | 11/2005 | Lapidus |
| 2006/0017957 A1 | 1/2006 | Degott et al. |
| 2006/0017959 A1 | 1/2006 | Downer et al. |
| 2006/0056695 A1 | 3/2006 | Wu et al. |
| 2006/0117465 A1 | 6/2006 | Willows et al. |
| 2006/0121181 A1 | 6/2006 | Sleat et al. |
| 2006/0199196 A1 | 9/2006 | O'Banion et al. |
| 2006/0286569 A1 | 12/2006 | Bar-Or et al. |
| 2007/0012784 A1 | 1/2007 | Mercolino |
| 2007/0026239 A1 | 2/2007 | Sigrist et al. |
| 2007/0041622 A1 | 2/2007 | Salva Calcagno |
| 2007/0048761 A1 | 3/2007 | Reep et al. |
| 2007/0072197 A1 | 3/2007 | Rayms-Keller et al. |
| 2007/0117119 A1 | 5/2007 | Akita et al. |
| 2007/0121937 A1 | 5/2007 | Kochevar et al. |
| 2007/0254292 A1 | 11/2007 | Fukasawa et al. |
| 2008/0038813 A1 | 2/2008 | Chen |
| 2008/0081357 A1 | 4/2008 | Kwon et al. |
| 2008/0149713 A1 | 6/2008 | Brundage |
| 2008/0153135 A1 | 6/2008 | Liu |
| 2008/0216255 A1 | 9/2008 | Poovey et al. |
| 2008/0290649 A1 | 11/2008 | Klein et al. |
| 2008/0293052 A1 | 11/2008 | Liang et al. |
| 2008/0299559 A1 | 12/2008 | Kwok et al. |
| 2008/0299667 A1 | 12/2008 | Kwok et al. |
| 2008/0312427 A1 | 12/2008 | Kwok et al. |
| 2009/0042191 A1 | 2/2009 | Hayward et al. |
| 2009/0057147 A1 | 3/2009 | Kayyem |
| 2009/0069199 A1 | 3/2009 | Brandenburg |
| 2009/0075261 A1 | 3/2009 | Hayward et al. |
| 2009/0136163 A1 | 5/2009 | Kerr et al. |
| 2009/0220789 A1 | 9/2009 | DeSimone et al. |
| 2009/0222912 A1 | 9/2009 | Boschin |
| 2009/0253127 A1 | 10/2009 | Gaudreau et al. |
| 2009/0286250 A1 | 11/2009 | Hayward et al. |
| 2009/0311555 A1 | 12/2009 | Badyal et al. |
| 2009/0313740 A1 | 12/2009 | Santos et al. |
| 2009/0325234 A1 | 12/2009 | Gregg et al. |
| 2010/0050344 A1 | 3/2010 | Peltz et al. |
| 2010/0065463 A1 | 3/2010 | Taylor |
| 2010/0075407 A1 | 3/2010 | Duffy et al. |
| 2010/0075858 A1 | 3/2010 | Davis et al. |
| 2010/0099080 A1 | 4/2010 | Church et al. |
| 2010/0149531 A1 | 6/2010 | Tang |
| 2010/0240101 A1 | 9/2010 | Lieberman et al. |
| 2010/0250616 A1 | 9/2010 | Kim |
| 2010/0258743 A1 | 10/2010 | Bortolin |
| 2010/0267091 A1 | 10/2010 | Murray et al. |
| 2010/0279282 A1 | 11/2010 | Liang et al. |
| 2010/0285447 A1 | 11/2010 | Walsh et al. |
| 2010/0285490 A1 | 11/2010 | Dees et al. |
| 2010/0285985 A1 | 11/2010 | Liang et al. |
| 2010/0307120 A1 | 12/2010 | Stover |
| 2011/0014133 A1 | 1/2011 | Grunstein |
| 2011/0046205 A1 | 2/2011 | Kosak et al. |
| 2011/0054938 A1 | 3/2011 | Hood et al. |
| 2011/0165569 A1 | 7/2011 | Macula |
| 2011/0229881 A1 | 9/2011 | Oshima et al. |
| 2011/0250594 A1 | 10/2011 | Liang et al. |
| 2011/0263688 A1 | 10/2011 | Barany et al. |
| 2012/0115154 A1 | 5/2012 | Hampikian |
| 2012/0264742 A1 | 10/2012 | Furuishi et al. |
| 2013/0040150 A1 | 2/2013 | Trexler et al. |
| 2013/0040381 A1 | 2/2013 | Gregg et al. |
| 2013/0046994 A1 | 2/2013 | Shaw |
| 2013/0048731 A1 | 2/2013 | Flickner et al. |
| 2013/0109596 A1 | 5/2013 | Peterson et al. |
| 2013/0149706 A1 | 6/2013 | Kwok et al. |
| 2013/0222559 A1 | 8/2013 | Lebaschi et al. |
| 2013/0234043 A1 | 9/2013 | Hussain et al. |
| 2013/0274129 A1 | 10/2013 | Katzen et al. |
| 2014/0099643 A1 | 4/2014 | Jung et al. |
| 2014/0106357 A1 | 4/2014 | Berrada et al. |
| 2014/0224673 A1 | 8/2014 | Alocilja |
| 2014/0256881 A1 | 9/2014 | Berrada et al. |
| 2014/0272097 A1 | 9/2014 | Jung et al. |
| 2014/0295423 A1 | 10/2014 | Liang et al. |
| 2015/0018538 A1 | 1/2015 | Berrada et al. |
| 2015/0030545 A1 | 1/2015 | Grass et al. |
| 2015/0083797 A1 | 3/2015 | Tran et al. |

(56) References Cited

U.S. PATENT DOCUMENTS

| | | |
|---|---|---|
| 2015/0104800 A1 | 4/2015 | Lee et al. |
| 2015/0107475 A1 | 4/2015 | Jung et al. |
| 2015/0110342 A1 | 4/2015 | Suzuki |
| 2015/0125949 A1 | 5/2015 | Liss |
| 2015/0133319 A1 | 5/2015 | Fu et al. |
| 2015/0141264 A1 | 5/2015 | Jung et al. |
| 2015/0191799 A1 | 7/2015 | Liang et al. |
| 2015/0232952 A1 | 8/2015 | Sun et al. |
| 2015/0266332 A1 | 9/2015 | Szczepanik et al. |
| 2015/0275271 A1 | 10/2015 | Berrada et al. |
| 2015/0302713 A1 | 10/2015 | Berrada et al. |
| 2015/0304109 A1 | 10/2015 | Tran et al. |
| 2015/0329856 A1 | 11/2015 | Liang et al. |
| 2016/0076088 A1 | 3/2016 | Tran et al. |
| 2016/0102215 A1 | 4/2016 | Hayward et al. |
| 2016/0168781 A1 | 6/2016 | Tran et al. |
| 2016/0246892 A1 | 8/2016 | Murrah et al. |
| 2016/0264687 A1 | 9/2016 | Tran |
| 2016/0326511 A1 | 11/2016 | Berrada et al. |
| 2016/0362723 A1 | 12/2016 | Jung et al. |
| 2017/0021611 A1 | 1/2017 | Jung et al. |

FOREIGN PATENT DOCUMENTS

| | | |
|---|---|---|
| EP | 0477220 B1 | 9/1996 |
| EP | 0840350 A2 | 5/1998 |
| EP | 1063286 A1 | 12/2000 |
| EP | 1231470 A1 | 8/2002 |
| EP | 1237327 A2 | 9/2002 |
| EP | 1403333 A1 | 3/2004 |
| EP | 1847316 A1 | 10/2007 |
| EP | 2428925 A1 | 3/2012 |
| EP | 2444136 A1 | 4/2012 |
| EP | 2444546 A1 | 4/2012 |
| GB | 2319337 A | 5/1998 |
| GB | 2434570 A | 8/2007 |
| JP | 63-503242 | 11/1988 |
| JP | 2009517250 A | 4/2009 |
| JP | 2011036278 A | 2/2011 |
| JP | 2013235553 A | 11/2013 |
| RU | 2084535 C1 | 7/1997 |
| RU | 2170084 C1 | 7/2001 |
| WO | 87/06383 A1 | 10/1987 |
| WO | 90/14441 A1 | 11/1990 |
| WO | 92/04469 A2 | 3/1992 |
| WO | 95/02702 A1 | 1/1995 |
| WO | 95/06249 A1 | 3/1995 |
| WO | 97/04392 A1 | 2/1997 |
| WO | 97/45539 A1 | 12/1997 |
| WO | 98/06084 A1 | 2/1998 |
| WO | 98/16313 A1 | 4/1998 |
| WO | 99/45514 A1 | 9/1999 |
| WO | 99/59011 A1 | 11/1999 |
| WO | 00/55609 A2 | 9/2000 |
| WO | 00/61799 A2 | 10/2000 |
| WO | 01/25002 A1 | 4/2001 |
| WO | 01/36676 A2 | 5/2001 |
| WO | 01/99063 A1 | 12/2001 |
| WO | 02/057548 A1 | 7/2002 |
| WO | 02/066678 A2 | 8/2002 |
| WO | 02/084617 A1 | 10/2002 |
| WO | 03/016558 A1 | 2/2003 |
| WO | 03/030129 A2 | 4/2003 |
| WO | 03/038000 A1 | 5/2003 |
| WO | 03/080931 A1 | 10/2003 |
| WO | 2004/025562 A1 | 3/2004 |
| WO | 2004/086323 A1 | 10/2004 |
| WO | 2005/075683 A1 | 8/2005 |
| WO | 2005/103226 A2 | 11/2005 |
| WO | 2006/109014 A1 | 10/2006 |
| WO | 2007/078833 A2 | 7/2007 |
| WO | 2008/007060 A1 | 1/2008 |
| WO | 2008045288 A2 | 4/2008 |
| WO | 2008/154931 A1 | 12/2008 |
| WO | 2009/027806 A1 | 3/2009 |
| WO | 2011/005222 A1 | 1/2011 |
| WO | 2012/076021 A1 | 6/2012 |
| WO | 2013/052924 A1 | 4/2013 |
| WO | 2013/154943 A1 | 10/2013 |
| WO | 2013/170009 A1 | 11/2013 |
| WO | 2014/062754 A1 | 4/2014 |
| WO | WO 2014006726 A1 | 6/2016 |

OTHER PUBLICATIONS

Skirtach, Andre, G. et al, "The Role of Metal Nanoparticles in Remote Release of Encapsulated Materials", Nano Letters, vol. 5, No. 7, 1371-1377 (2005).
Fixe, F. et al., Thin Film Micro Arrays with Immobilized DNA for Hybridization Analysis, Mat. Res. Soc. Symp. Proc. vol. 723, Materials Research Society, O2.3.1-O2.3.6 (2002).
Hayward, Jim et al., "A Scaled, Integrative Implementation for DNA Marking of Integrated Circuits", Applied DNA Sciences, 1-25 (2013).
Ovsianikov, Aleksandr et al., "Two-Photon Polymerization Technique for Microfabrication of CAD-Designed 3D Scaffolds from Commercially Available Photosensitive Materials", Journal of Tissue Engineering and Regenerative Medicine, 1:443-449 (2007).
Khandjian, E.W., "Optimized Hybridization of DNA Blotted and Fixed To Nitrocellulose and Nylon Membranes" Biotechnology, vol. 5, 165-167 (1987).
Chrisey, Linda A et al., "Fabrication of Patterned DNA Surfaces", Nucleic Acids Research, vol. 24, No. 15, 3040-3047 (1996).
Wollenberger, Louis V. et al., "Detection of DNA Using Upconverting Phosphor Reporter Probes", SPIE, vol. 2985, 100-111 (1997).
Takara Bio, "Takara Bio to Produce DNA Fragments for DNA Microarrays on Industrial Scale", http://www.evaluategroup.com/Universal/View.aspx?type_Story&id.
Obeid, Pierre J. et al., "Microfabricated Device for DNA and RNA Amplification by Continuous-Flow Polymerase Chain Reaction and Reverse Transcription-Polymerase Chain Reaction with Cycle Number Section", Anal. Chem, 75, 288-295 (2003).
Supplemental European Search Report for Corresponding European Patent Application No. EP14820538.8, pp. 1-8 (dated Jan. 25, 2017).
Hashimoto, Masahiko et al., "Rapid PCR in a Continuous Flow Device", Lab Chip, 4, 638-645 (2004).
Thibaudau, Franck, "Ultrafast Photothermal Release of DNA from Gold Nanoparticles", J. Phys. Chem. Lett. 3, 902-907 (2012).
Berger, S.A. et al., "Flow in Curved Pipes", Ann. Rev. Fluid Mech., 15:461-512 (1983).
Written Opinion of the International Search Authority for PCT/US2015/013084 dated Apr. 17, 2015.
Ageno, M., et al., "The Alkaline Denaturation of DNA", Biophys J., Nov. 1969; 9(11): 1281-1311.
Hou, Sen, et al., "Method to Improve DNA Condensation Efficiency by Alkali Treatment", Taylor & Francis, Nucleosides, Nucleotides and Nucleic Acids, 28:725-735, 2009.
Thiel, Teresa, et al., "New zwitterionic butanesulfonic acids that extend the alkaline range of four families of good buffers: Evaluation for use in biological systems", J. Biochem. Biophys., Methods 37 (1998) 117-129.
Schulz, M.M., et al., "Archived or directly swabbed latent fingerprints as a DNA source for STR typing", Forensic Science International 127 (2002) 128-130.
Park, H., et al., "Stress response of fibroblasts adherent to the surface of plasma-treated poly(lactic-co-glycolic acid) nanofiber matrices", Colloids Surf B Biointerfaces, May 1, 2010, 1;77(1); 90-5.
WiseGeek, "How Many Species of Bacteria Are There", http://www.wisegeek.org/how-many-species-of-bacteria-are-there.htm.
Wikipedia, "List of sequenced bacterial genomes", http://en.wikipedia.org/wiki/List_of_sequenced_bacterial_genomes.
Wikipedia, "Virus", http://en.wikipedia.org/wiki/Virus.
Agrawal, Sudhir, et al., "Site-Specific Functionalization of Oligodeoxynucleotides for Non-Radioactive Labelling", Tetrahedron Letters, vol. 31, No. 11, pp. 1543-1546, 1990.

(56) References Cited

OTHER PUBLICATIONS

Beija, Mariana, et al., "Synthesis and applications of Rhodamine derivatives as fluorescent probes", Chem. Soc. Rev., 2009, 38, 2410-2433.
Corstjens, P.L.A.M., et al., "Infrared up-converting phosphors for bioassays", IEE Proc.—Nanobiotechnol., vol. 152, No. 2, Apr. 2005.
Tyagi, Sanjay, et al., "Multicolor molecular beacons for allele discrimination", Nature Biotechnology, vol. 16, Jan. 1996.
Gibson, U.E., et al., "A novel method for real time quantitative RT-PCR", Genome Res., 1996, 6:995-1001.
Gupta, K.C., et al., "A general method for the synthesis of 3'-sulfhydryl and phosphate group containing oligonucleotides", Nucleic Acids Research, vol. 19, No. 11, p. 3019-3025 (1991).
Heid, C.A., et al., "Real time quantitative PCR", Genome Res. 1996 6:986-994.
Holland, Pamela, M., et al., "Detection of specific polymerase chain reaction product by utilizing the 5'→3' exonuclease activity of Thermus aquaticus DNA polymerase", Proc. Natl. Acad. Sci. USA, vol. 88, pp. 7276-7280, Aug. 1991, Biochemistry.
Hosokawa, Kazuo, et al., "DNA Detection on a Power-free Microchip with Laminar Flow-assisted Dendritic Amplification", Analytical Sciences, Oct. 2010, vol. 26.
Hussein, Ebtissam, H.A., et al., "Molecular Characterization of Cotton Genotypes Using PCR-based Markers", Journal of Applied Sciences Research, 3(10): 1156-1169, 2007.
Ibrahim, Rashid Ismael Hag, et al., "Complete Nucleotide Sequence of the Cotton (*Gossypium barbadense* L.) Chloroplast Genome with a Comparative Analysis of Sequences among 9 Dicot Plants", Genes Genet. Syst. (2006) 81, p. 311-321.
Jiang, Chun-Xiao, et al., "Polyploid formation created unique avenues for response to selection in Gossypium (cotton)", Proc. Natl. Acad. Sci. USA, vol. 95, pp. 4419-4424, Apr. 1998.
Kaneda, Shohei, et al., "Modification of the Glass Surface Property in PDMS—Glass Hybrid Microfluidic Devices", Analytical Sciences, Jan. 2012, vol. 28.
Karahan, H.A., et al., "Improvements of Surface Functionality of Cotton Fibers by Atmospheric Plasma Treatment", Fibers and Polymers 2008, vol. 9, No. 1, 21-26.
Lee, Seung-Bum, et al., "The complete chloroplast genome sequence of Gossypium hirsutum: organization and phylogenetic relationships to other angiosperms", BMC Genomics 2006, 7:61.
Lee, Linda G., et al., "Allelic discrimination by nick-translation PCR with fluorogenic probes", Nucleic Acids Research, 1993, vol. 21, No. 16, 3761-3766.
Tyagi, Sanjay, et al., "Molecular Beacons: Probes that Fluoresce upon Hybridization", Nature Biotechnology, vol. 18, Mar. 1996.
Sproat, Brian S. et al., "The synthesis of protected 5'-mercapto-2', 5'-dideoxyribonucleoside-3'-O-phosphoramidites; uses of 5'-mercapto-oligodeoxyribonucleotides", Nucleic Acids Research, vol. 15, No. 12, 1987.
Nazarenko, I.A., et al., "A closed tube format for amplification and detection of DNA based on energy transfer", Nucleic Acids Research, 1997, vol. 25, No. 12, 2516-2521.
Nelson, Paul S., et al., "Bifunctional oligonucleotide probes synthesized using a novel CPG support are able to detect single base pair mutations", Nucleic Acids Research, vol. 17, No. 18, 1989.
International Preliminary Report on Patentability issued in PCT/US2013/065161 dated Apr. 21, 2015.
Written Opinion of the International Searching Authority issued in PCT/US15/21165 dated Jul. 2, 2015.
Tuzlakoglu, K., et al., "A new route to produce starch-based fiber mesh scaffolds by wet spinning and subsequent surface modification as a way to improve cell attachment and proliferation", Journal of Biomedical Materials Research Part A, 2009, Wiley Periodicals, Inc, p. 369-377.
Zuckermann, Ronald, et al., "Efficient methods for attachment of thiol specific probes to the 3'-ends of synthetic oligodeoxyribonucleotides", Nucleic Acids Research, vol. 15, No. 13, 1987.
Yang, XF, et al., "Fluorimetric determination of hemoglobin using spiro form rhodamine B hydrazide in a micellar medium", Talanta Nov. 12, 2003; 61(4): 439-45.
Ullrich, Thomas, et al., "Competitive Reporter Monitored Amplification (CMA)—Quantification of Molecular Targets by Real Time Monitoring of Competitive Reporter Hybridization", Plos One, Apr. 2012, vol. 7, Issue 4.
Van de Rijke, Frans, et al., "Up-converting phosphor reporters for nucleic acid microarrays", Nature Publishing Group, Nature Biotechnology 19, Mar. 2001, 273-276.
Whitcombe, David, et al., "Detection of PCR products using self-probing amplicons and fluorescence", Nature Biotechnology, vol. 17, Aug. 1999, p. 804-807.
Hunicke-Smith, Scott P., "PCR and Cycle Sequencing Reactions: A New Device and Engineering Model", Dissertation, Stanford University, pp. i-xiv and 1-200, May 1997.
Extended European Search Report issued in European Patent Application No. 14852842.5 dated Jun. 12, 2017.

* cited by examiner

COMPOSITION AND METHOD OF DNA MARKING ELASTOMERIC MATERIAL

CROSS-REFERENCE TO RELATED APPLICATION

The present application claims the benefit of U.S. Provisional Application Ser. No. 62/407,819 filed on Oct. 13, 2016, which is herein incorporated by reference in its entirety.

STATEMENT OF GOVERNMENT LICENSE RIGHTS

This invention was made with Government support under the Rapid Innovation Fund contract number, HQ0147-14-C-8019, awarded by the U.S. Office of Secretary of Defense and managed by the U.S. Defense Logistics Agency. The Government has certain rights in the invention.

BACKGROUND OF THE INVENTION

In recent years, deoxyribonucleic acid (DNA) molecules have been synthesized to include any useful set of information as encoded via the ordinary DNA building blocks A, T, C, and G. George Church at Harvard and other labs around the world, have recently shown that this well-known genetic code, which is used in nature to encode the core information of life can instead be used in a biotech context to encode ordinary alphanumeric information. The nucleic acid building blocks A, T, C, and G from which DNA is made comprising a N=4 (quaternary) digital code, much as bars on an ordinary bar code comprise an N=2 (binary) digital code.

Based on that simple idea to convert DNA information (A, T, C, and G) into an equivalent alphanumeric code, it has been shown over the past 10 years that DNA can be a medium for extremely high density data storage. A number of standard "DNA alphabets" have been discussed, which relate each of the possible 64 base triplets (e.g. A,T,C) to a single letter or number, thus allowing any alphanumeric symbol to be converted to an equivalent triplet based DNA code.

There is a growing need to be able to provide information within objects used in various settings such as household items or military and commercial parts in a manner that does not change the overall characteristics of the item. For example, many items are used by the military which include parts made of elastomeric material such as silicone rubber. There is a need to place information within these parts that can be accessible by commercially available means and without exorbitant cost. The amount of information included with the item could be small or great, such as providing an item number, country of origin, or information regarding the intended use of the object.

There is also a need to add coded DNA to elastomeric materials in a way which will protect the DNA during exposure to high temperatures associated with molding and curing elastomeric materials.

SUMMARY OF THE INVENTION

In one embodiment, the invention relates to a method of incorporating DNA into an elastomeric material. The method includes the steps of (1) treating DNA with an additive to form a treated DNA, wherein the additive is a polyol, diol, glycol, starch, or pyrrolidone; (2) mixing the treated DNA with an elastomeric material to form a mixture; (3) molding the mixture; and (4) curing the mixture.

Preferably, the elastomeric material is liquid silicone rubber. The preferred additives are polyols. Preferred polyols are polyethylene glycol and methylated polyethylene glycol.

Preferably, the treated DNA is mixed with liquid silicone colorant prior to being added to uncolored liquid silicone rubber base.

In another embodiment, the invention relates to a method of incorporating DNA into a silicone-metal composite material. The method includes the steps of (1) mixing DNA with metal microspheres to form a first mixture; (2) mixing the first mixture with a silicone material to form a second mixture; (3) molding the second mixture; and (4) curing the second mixture to form a silicone-metal composite material.

The mixture may be cured at temperatures equal to or greater than about 150° C. Curing can take place by press curing and post curing. Types of molding include press molding, injection molding, and blow molding.

Preferably, the ratio of the first mixture to the silicone material is between about 1:1 to about 10:1. The metal microspheres preferably include silver-plated copper.

In another embodiment, the invention relates to a method of recovering information within a silicone object with embedded, coded DNA. The method includes the steps of (1) providing a silicone object with embedded, coded DNA; (2) isolating coded DNA from the silicone object; (3) sequencing the coded DNA; and (4) decoding the sequence.

Preferably, the coded DNA is recovered by washing the silicone object with solvent comprising methyl ethyl ketone and dichloromethane; removing excess solvent; using a commercially available kit to isolate the coded DNA; and amplifying the coded DNA by polymerase chain reaction.

Another embodiment of the invention relates to a method of authenticating a silicone object with embedded DNA. The method includes the steps of providing a silicone object with embedded DNA; recovering the DNA from the silicone object; and verifying the authenticity of the object by identifying the DNA. The DNA may be recovered as indicated above.

A composition including encoded DNA embedded within an elastomeric material is also claimed.

DETAILED DESCRIPTION

The present invention relates to a method of incorporating DNA into elastomeric material. Elastomeric materials include, but are not limited to, unsaturated rubbers, saturated rubbers, and other types of 4S elastomers.

Examples of unsaturated rubbers include natural polyisoprene: cis-1,4-polyisoprene natural rubber (NR) and trans-1,4-polyisoprene gutta-percha; synthetic polyisoprene (IR for isoprene rubber); polybutadiene (BR for butadiene rubber); chloroprene rubber (CR), polychloroprene, Neoprene, Baypren etc.; butyl rubber (copolymer of isobutylene and isoprene, UR); halogenated butyl rubbers (chloro butyl rubber: CIIR; bromo butyl rubber: BIIR); styrene-butadiene Rubber (copolymer of styrene and butadiene, SBR); nitrile rubber (copolymer of butadiene and acrylonitrile, NBR), also called Buna N rubbers; and hydrogenated nitrile rubbers (HNBR) Therban and Zetpol.

Examples of saturated rubbers include EPM (ethylene propylene rubber, a copolymer of ethylene and propylene) and EPDM rubber (ethylene propylene diene rubber, a terpolymer of ethylene, propylene and a diene-component); epichlorohydrin rubber (ECO); polyacrylic rubber (ACM, ABR); silicone rubber (SI, Q, VMQ); fluorosilicone rubber (FVMQ); fluoroelastomers (FKM, and FEPM) Viton, Tecnoflon, Fluorel, Aflas and Dai-El; perfluoroelastomers (FFKM) Tecnoflon PFR, Kalrez, Chemraz, Perlast; polyether block amides (PEBA); chlorosulfonated polyethylene (CSM), (Hypalon); and ethylene-vinyl acetate (EVA).

Other types of elastomers include other types of 4S elastomers such as thermoplastic elastomers (TPE); the proteins resilin and elastin; polysulfide rubber; and elastolefin.

The preferred elastomeric material is silicone rubber. Forms of silicone rubber include, but are not limited to, liquid silicone rubber (LSR) and silicone metal-composite materials such as silver coated copper microspheres in silicone.

DNA can be incorporated into LSR by first treating the DNA with an additive. Methods of treating DNA to increase its recovery from objects was disclosed in U.S. Pat. No. 9,297,032 to Jung, et al. which is incorporated herein by reference. Jung, et al. treat the DNA with various additives which Jung, et al. refer to as "perturbants" to increase the recoverability of the DNA taggant. Additives also provide a means of suspending the DNA in a water-free, miscible solution.

Additives include, but are not limited to, a polyol or a diol or glycol, a starch or a pyrrolidone. The polyol can be any suitable polyol, such as a polyethylene glycol polymer (PEG), for instance a PEG 200, i.e., a polyethylene glycol having an average molecular number of 200 ethylene glycol units per chain (such as the PEG200 Mn 200 Product No. P3015), Sigma-Aldrich, St. Louis, Mo. Alternatively, in another embodiment, the polyethylene glycol can be a PEG 10,000 polyol polymer such as the PEG10,000 Product No. P3015, Mn 10,000 from Sigma-Aldrich. Any of the PEGs may be methylated. The preferred additives are methylated PEG and un-methylated PEG.

The glycol useful as an additive can be any suitable glycol or diol, such as for instance, ethylene glycol, diethylene glycol, glycerol, methanediol, triethylene glycol, propylene glycol from Sigma-Aldrich, or 1,2-butanediol or 1,4-butanediol from Fluka Analytical.

The starch can be, for example, a hydroxypropyl starch such as Zeina® B860 from Grain Processing Corp., Muscatine, Iowa. In still another embodiment, the pyrrolidone additive of the invention can be any suitable pyrrolidone such as, for instance, an N-alkyl pyrrolidone, or the caprylyl pyrrolidone surfactant: Surfadone® LP100 available from Ashland Inc., Covington, Ky.

The treated DNA is mixed with LSR under conditions and duration determined by a person having skill in the art to ensure uniformity of the mixture. A preferred ratio of DNA to LSR is about less than 1 ppm, i.e, less than $1 \times 10^{-6}$ by mass. The mixture can then be molded by any means in the art to create the desired product.

Types of molding include press molding into a form, injection molding, and blow molding. For example, the mixture can be press molded or injection molded to create O-rings, gaskets, and various sealant parts.

The molded parts are subsequently cured as determined by a person having ordinary skill in the art. Curing take place at elevated temperatures for prolonged periods. For example, curing can take place at temperatures from about 150° C. to about 250° C., for up to about 5 hours, depending upon the application. Curing may also take place in two steps—(1) using a molding press to heat cure and (2) post curing in an oven at elevated temperatures for several hours. In one example, heat curing may take place at temperatures of about 150° C. for a few minutes, while post-curing may occur in an oven maintaining temperatures of around 200° C. for four or more hours.

A preferred aspect of the invention involves first mixing the treated DNA with a liquid silicone colorant then adding treated DNA to an uncolored liquid silicone rubber base.

Another embodiment of the invention relates to a method of incorporating DNA into a silicone-metal composite material. The method involves mixing either untreated or treated DNA with metal microspheres to form a first mixture under conditions appropriate for the DNA to adhere to the metal microspheres. The metal microsphere can be any metal microspheres known in that art. For example, the metal microspheres may comprise silver-plated copper.

The DNA adhered metal microspheres may then be incorporated into a silicone material to form a second mixture by any means known in the art such as by blender or mixer. A preferred silicone-composite material is silver plated copper filled silicone. The second mixture may then be molded and cured under conditions well known in the art. For example, curing may take place at about 200° C. for a minimum of about 5 minutes, 10 minutes, 1 hour, 2 hours, 3 hours, or 4 hours and for a maximum of about 2 hours, 3 hours, 4 hours, 5 hours, and 6 hours. Each minima may be combined with each maxima to create a range.

The ratio of the DNA adhered metal microspheres (first mixture) to the silicone material may be about 1:1 to about 10:1. Enough DNA must be present so that a person having ordinary skill would be able to easily extract DNA from the cured silicone object and sequence the DNA.

Another embodiment of the invention includes a method of recovering information within a silicone object with embedded, coded DNA. Coded DNA includes DNA that has been synthesized to include information within its sequence. For example, a "DNA alphabet" may be used which assigns a single letter or number to each of the possible 64 base triplets, e.g. A,T,C, to allow any alphanumeric symbol to be converted into an equivalent triplet based DNA code.

The coded DNA within the silicone object may be recovered by first washing the silicone object with solvent comprising methyl ethyl ketone and dichloromethane. Excess solvent is removed. Commercially available kits may be utilized to isolate the coded DNA. Finally, the coded DNA is amplified by polymerase chain reaction. Then, the DNA may be sequenced and the sequence may be decoded to recover the embedded information.

Another embodiment of the invention includes a method of authenticating a silicone object with embedded DNA. The method includes the steps of providing a silicone object with embedded DNA, recovering the DNA from the silicone object, and verifying the authenticity of the object by identifying the DNA.

Another embodiment of the invention relates to a composition including an encoded DNA in an elastomeric material. The methods of making the composition are described above.

EXAMPLES

Examples have been set forth below for the purpose of illustration and to describe the best mode of the invention at the present time. The scope of the invention is not to be in any way limited by the examples set forth herein.

Example 1

DNA Manufacture

A DNA concentrate comprising two different DNAs of different lengths, A and B, was prepared via large scale preparative Polymerase Chain Reaction (PCR). The resulting DNA was formulated with an emulsifier to provide for a stable emulsion formation in a non-aqueous silicone matrix containing both DNAs. Three separate vials were prepared with 2 mL of DNA that were suitable for a direct addition to the silicon fabrication process.

Example 2

DNA Blending into Liquid Silicone Rubber (LSR)

One batch of LSR colorant (GSDI Silicopas, Red345) was chosen for the manufacturing process. Each vial of the DNA concentrate (2 mL) was added to 500 grams of the LSR colorant and mixed with a mechanical propeller for a total of 45 minutes. Samples (1 mL) were taken at the end of the mixing, to test for blending uniformity. Samples from the mixing process were collected and DNA analyzed in triplicate (See Table I).

Once blending uniformity was confirmed, the resulting DNA-Silicopas colorant mixture was then blended at $\frac{1}{20}$ with an uncolored GSDI silicone base (ELASTOSIL LR 3003 A, B US). The silicone was then injection molded using a Fluid Automation Meter Mix System and a Boy 55E molding press (www.boymachines.com) to heat cure and mold into O-rings, gaskets, and various sealant parts. Upon molding and curing (including post cure at 200° C. for four hours) molded parts were authenticated (See Table II).

Example 3

DNA Blending into Conductive Silicone-Metal Composite Material

One vial of DNA concentrate (2 ml) was blended into silver coated copper microspheres for 1 minute and then mixed into a 10 lbs. mixture of SAS SEALTRON® 1068 (Silver Plated Copper filled Silicone, 85A Durometer) for 47 minutes to yield 10 lbs. of DNA embedded SAS SEALTRON® 1068. Following the mixing procedure, the DNA embedded SEALTRON® 1068 was apportioned to individual gasket molds for thermal curing. Each gasket was press cured for approximately 10 minutes at 150° C. and then post cured for several hours at 200° C. per standard specifications. The DNA embedded raw (uncured) material, and cured parts at different time points were analyzed (See Table III). In addition, DNA tagged EMI shielding parts and controls were submitted to ASTM and MIL-DTL testing at independent laboratories.

Example 4

DNA Extraction from Heat Cured Silicone Parts

Molded, heat cured silicone parts were cut into small pieces and then washed in a mixture of 2 mL of MEK (methyl ethyl ketone) and 2 mL of DCM (dichloromethane) for 1 hour at 55° C. Excess solvent was removed by pipetting and the washed parts were dried for 15 minutes at 90° C. DNA was extracted from the surface of the washed parts via the Extraction and Dilution (E&D) method and purified with ChargeSwitch magnetic beads (Life Tech). In some cases, a fragment of the silicone part was placed directly into the PCR reaction (i.e. in situ PCR) then amplified directly as described above.

Example 5

Analysis by PCR-CE After DNA Recovery from Silicone Parts

The extracted DNA from all DNA embedded silicone parts was PCR amplified per a standard protocol. Briefly, 40 Cycles of amplification was performed using the DNA extraction from the heat cured silicone parts as the template. The amplified DNA was labeled with the fluorescent FAM (or HEX) dye linked to the specific PCR primers. After amplification, the resulting DNA was then analyzed using capillary electrophoresis (CE) analysis where the target DNA was detected via the FAM (or HEX) fluorescent label, under conditions where fragment length could be resolved to +/−1 base pair resolution. In the representative CE traces the two colors associated with each DNA peak identify two different DNA clones deployed.

Example 6

Physical Testing of DNA-Marked Silicone Microsphere Composites

D.L.S Electronic Systems and Akron Rubber Development Labs (ARDL) were chosen for independent physical testing of the DNA-embedded silicone gaskets for testing in accordance with MIL-DTL 83528 and ASTM test methods. Subsequent to the required testing, the parts were exposed to tensile, tear strength, and durometer tests, and then the DNA was recovered and analyzed (See Table IV, V).

Example 7

Physical Testing of DNA-Marked LSR Silicone Parts and Controls

Akron Rubber Development Labs (ARDL) was chosen for independent physical testing of the DNA-embedded silicone gaskets for testing in accordance with ASTM test methods. Subsequent to the required testing, the parts were exposed to tensile, tear strength, and durometer tests, and then the DNA was recovered and analyzed (See Table X, XI).

Example 8

Results

Analysis of DNA Uniformity in LSR GSDI Silicopas Red 345 Colorant Prior to Injection Molding and Heat-Curing As seen in Table I, DNA was successfully recovered from the uncured fluid LSR Silicopas colorant, subsequent to 45 minutes of mixing. Each DNA-mixed colorant sample was tested twice for DNA extraction, and each extracted DNA sample was tested in triplicate, totaling six replicate for each sample. After DNA was extracted, from 50 mg of material, it was then diluted to 1:100K for testing. Both DNA taggants were detected in all samples.

These results indicate that good DNA homogeneity was obtained in the fluid colorant after 45 minutes of mixing. Subsequent to DNA mixing, the DNA embedded Red 345 colorant was transferred to SAS, and blended $\frac{1}{20}$ with colorless silicone base and then injection molded.

DNA Analysis of Cured, Injection Molded LSR Parts

DNA marked LSR parts were authenticated by PCR-CE (4). Prior to the 4 hour heat curing, samples were collected and in situ PCR was performed. Post 4 hour curing, both E&D extraction and in situ PCR were performed in triplicate. All samples resulted in successful detection of intact DNA, as shown in Table II.

Intact DNA Detection from Heat-Cured, Conductive Silicone-Metal Microsphere Composites Four types of samples were received for this category: uncured, 8 minute and 15 minute heat-cured (150° C.) and several hour heat-cure samples (200° C.). Each sample was tested in triplicate. As seen in Table III, DNA was successfully recovered and authenticated in all samples.

Repeat of DNA Analysis, Subsequent to Third Party Physical Testing

Cured LSR and conductive composite parts were subjected to third party physical testing. Subsequent to that physical testing, the parts were returned to Applied DNA Sciences and subjected to repeat of DNA recovery and analysis. As seen in Tables IV and V, it was found that intact DNA was recovered and detected in all parts.

DNA Sequence Analysis of Intact DNA Recovery from Heat Cured LSR Parts

Intact DNA was recovered from heat cured LSR parts, subsequent to several hours of heat curing at 200° C. (Table II, IV). The inventors tried to determine if the two DNAs comprising the DNA mark could be analyzed via full sequence analysis.

Each of the two DNAs used were amplified by a unique pair of PCR primers, allowing each to be subjected to PCR, and then followed by standard Sanger chain terminator sequencing. The resulting sequence data for the center most bp segment of each DNA are shown in Table XI, the terminal regions of each being excluded because those sequence data are in general too close to the origin defined by sequencing primers to be useful.

This small set of pilot data revealed no sequencing errors in the central domain of DNA 1 (of specified segment length A), whereas the longer mark, DNA 2 (of specified segment length B) showed 7 sequencing errors in its central domain. The process of blending DNA into silicone and subjecting the parts to ordinary heat curing at 200° C., has begun to yield an adequate measure of the detailed sequence of each of the two DNAs which had been blended into the silicone parts.

CONCLUSION

A pair of DNAs, of different lengths, were formulated so that they could be mixed with liquid silicone (GSDI Silicopas Colorant) and microsphere composites containing silicone, copper, and silver (SAS Sealtron® 1068) then molded and heat cured to generate parts that could be used for military and aerospace applications. After molding and heat curing, DNA was extracted and authenticated positively from all molded heat cured LSR parts and from all molded and cured DNA-embedded SAS Sealtron® 1068 parts.

It was shown that the DNA thus recovered remained intact with respect to ordinary DNA analysis (PCR-CE) and at a somewhat higher level of sophistication could be subjected to detailed DNA sequence analysis, thus raising the possibility that DNA may now be considered as a method to introduce both a molecular mark to authenticate heat cured silicone and silicone-metal composites and as a way to encode explicit part-related information into such DNAs: so that the molecularly encoded information may be linked, physically, to the material during its use in the supply chain, thereafter.

Example 9

Tables

TABLE I

DNA authentication results from the DNA-mixed LSR Colorant before curing

| | | | DNA authentication results | |
| | | | DNA 1 specified length A | DNA 2 specified length B |
| Sample | Sample # | Replicate | Peak height | Peak height |
| Red 345 Colorant | 1 | 1 | 32720 | 32714 |
| | | 2 | 32726 | 32762 |
| | | 3 | 32733 | 32704 |
| | 2 | 1 | 32712 | 32765 |
| | | 2 | 32722 | 32740 |
| | | 3 | 32691 | 32742 |
| Positive control | | | 32710 | 32766 |
| Negative control | | | — | — |

TABLE II

Intact DNA detection from heat-cured LSR parts

| | | | DNA authentication results | |
| | | | DNA 1 specified length A | DNA 2 specified length B |
| Sample | Extraction method | Replicate test | Peak height | Peak height |
| Before curing | in situ | 1 | 32721 | 32766 |
| | | 2 | 26318 | 32764 |
| | | 3 | 32713 | 32766 |
| Curing for 4 hrs, 200° C. | EnD | 1 | 12748 | 32766 |
| | | 2 | 17102 | 32747 |
| | | 3 | 32703 | 32760 |
| | in situ | 1 | 2885 | 32765 |
| | | 2 | 6067 | 32758 |
| | | 3 | 6184 | 32708 |
| Positive control | | | 32744 | 32763 |
| Negative control | | | — | — |

TABLE III

Intact DNA detection from the heat-cured Conductive Silicone-Metal Composite Material

| | | | DNA authentication results | |
| | | | DNA 1 specified length A | DNA 2 specified length B |
| Sample | Sample# | Replicate | Peak height | Peak height |
| Uncured | Sample 1 | 1 | 32709 | 32707 |
| | | 2 | 32714 | 32721 |
| | | 3 | 32738 | 32765 |
| Cured 8 min, 150° C. | Sample 1 | 1 | 6934 | 32762 |
| | | 2 | 6983 | 32764 |
| | | 3 | 3168 | 32728 |
| Cured 15 min, 150° C. | Sample 1 | 1 | 32761 | 32764 |
| | | 2 | 32762 | 32765 |
| | | 3 | 32719 | 32766 |

TABLE III-continued

Intact DNA detection from the heat-cured Conductive Silicone-Metal Composite Material

| | | | DNA authentication results | |
|---|---|---|---|---|
| | | | DNA 1 specified length A | DNA 2 specified length B |
| Sample | Sample# | Replicate | Peak height | Peak height |
| Post-Cured several hours, 200° C. | Sample 1 | 1 | 24592 | 32719 |
| | | 2 | 11717 | 32766 |
| | | 3 | 32683 | 32692 |
| | Sample 2 | 1 | 20644 | 32766 |
| | | 2 | 10007 | 32708 |
| | | 3 | 32716 | 32766 |
| DNA Concentrate Residual | | | 32744 | 32763 |
| Negative control | | | — | — |

TABLE IV

Intact DNA detection from the cured LSRs: After independent physical testing

| | | | DNA authentication results | |
|---|---|---|---|---|
| | | | DNA 1 specified length A | DNA 2 specified length B |
| Sample | Extraction method | Replicate test | Peak height | Peak height |
| Strip for the tear strength test | E&D | 1 | 8435 | 32766 |
| | | 2 | 9246 | 32767 |
| | | 3 | 14448 | 32731 |
| Strip for the tensile and elongation tests | E&D | 1 | 12000 | 32766 |
| | | 2 | 15829 | 32766 |
| | | 3 | 24963 | 32764 |
| Plug for the durometer and specific gravity test | E&D | 1 | 15649 | 32765 |
| | | 2 | 7758 | 32766 |
| | | 3 | 8687 | 32718 |
| Positive control | | | 32744 | 32763 |
| Negative control | | | — | — |

TABLE V

Intact DNA detection from conductive silicon microsphere composites: After independent physical testing

| | | DNA authentication results | |
|---|---|---|---|
| | | DNA 1 | DNA 2 |
| Sample | Replicate | Peak height | Peak height |
| DNA infused electrically conductive elastomer gasket (MIL-DTL-83528E4.5.12) | 1 | 4950 | 32607 |
| | 2 | 4247 | 26042 |
| | 3 | 7254 | 24085 |
| DNA infused conductive rubber strips for the tear strength test (ASTM D 624-2012) | 1 | 547 | 32408 |
| | 2 | 1962 | 32592 |
| | 3 | 1278 | 32492 |
| DNA infused conductive rubber strips for the tensile and elongation tests (ASTM D412-15a) | 1 | 1296 | 7826 |
| | 2 | 616 | 15128 |
| | 3 | 343 | 10141 |
| DNA infused conductive rubber strips for the durometer (ASTM D 2240-15) and specific gravity (ASTM D 792-13) | 1 | 348 | 10468 |
| | 2 | 371 | 13015 |
| | 3 | 2500 | 32719 |
| Positive control | 1 | 32697 | 32705 |
| Negative control | 1 | — | — |

TABLE VI

Physical Testing Results, Silicone Composite:
D.L.S Electronic Systems, Inc.
Test Specification: MIL-DTL-83528E

| Material | Minimum attenuation level (dB) | Best-case attenuation level (dB) | Outcome |
|---|---|---|---|
| 1068-Control Type K - Electrically conductive elastomer (EcE) | 117@20 MHz | 146@400 MHz | Pass |
| 1068-With DNA Type K - Electrically conductive elastomer (EcE) | 114@20 MHz | 147@400 MHz | Pass |

TABLE VII

Physical Testing Results, Silicone Composite:
D.L.S Electronic Systems, Inc.
Test Specification: MIL-DTL-83528E

| Shielding effectiveness frequency | Dynamic range | 1068-Control (SE) | 1068-DNA (SE) | Outcome |
|---|---|---|---|---|
| 20 | 130 | 117 | 114 | Pass |
| 30 | 140 | 129 | 129 | Pass |
| 40 | 140 | 133 | 133 | Pass |
| 60 | 140 | 135 | 134 | Pass |
| 80 | 140 | 137 | 136 | Pass |
| 100 | 140 | 136 | 137 | Pass |
| 200 | 140 | 135 | 135 | Pass |
| 400 | 150 | 146 | 147 | Pass |
| 600 | 150 | 140 | 139 | Pass |
| 800 | 150 | 143 | 141 | Pass |
| 1000 | 150 | 142 | 144 | Pass |
| 2000 | 122 | 120 | 118 | Pass |
| 4000 | 122 | 119 | 118 | Pass |
| 6000 | 122 | 118 | 117 | Pass |
| 8000 | 122 | 118 | 118 | Pass |
| 10000 | 122 | 120 | 117 | Pass |

TABLE VIII

Physical Testing Results from ARDL Conductive Silicone-Metal Composite Material
Test Specification: Original Physical Properties, ASTM D 412-15a, D 2240-15, D 792-13

Material
Die C dumbells tested at 20 in/min
Type A durometer measured on buttons

| | Minimum attenuation level (dB) | | | Best-case attenuation level (dB) | | | Outcome |
|---|---|---|---|---|---|---|---|
| Type A durometer, points | 87 | 83 | 85 | 90 | 90 | 90 | Pass |
| Tensile strength, psi | 492 | 454 | 486 | 475 | 472 | 474 | Pass |
| 100% Modulus, psi | 276 | 270 | 266 | — | — | — | Pass |
| 200% Modulus, psi | 407 | 408 | 421 | — | — | — | Pass |
| Specific gravity | 3.532 | 3.524 | 3.528 | 3.284 | 3.300 | 3.290 | Pass |

TABLE IX

Physical Testing Results from ARDL
Conductive Silicone-Metal Composite Material
Test Specification: Tear Resistance, ASTM D 624-2012

Material
Tear specimens tested at 20 in/min

| | 1068-Control | | | 1068-DNA | | | Outcome |
|---|---|---|---|---|---|---|---|
| Tear strength, ppi | 49 | 44 | 46 | 68 | 70 | 68 | Pass |

TABLE X

Physical Testing Results from ARDL Liquid Silicone Rubber Composites
Test Specification: Original Physical Properties, ASTM D 412-15a, D 2240-15, D792-13

Material
Die C dumbells tested at 20 in/min

| | Samples containing no DNA | | | Samples containing DNA | | | Outcome |
|---|---|---|---|---|---|---|---|
| | Sample # | | | | | | |
| | 013 | 014 | 015 | 004 | 005 | 006 | |
| Tensile strength, psi | 1473 | 1467 | 1579 | 1527 | 1582 | 1346 | Pass |
| Ultimate elongation, % | 429 | 495 | 508 | 468 | 482 | 417 | |
| 100% Modulus, psi | 290 | 245 | 257 | 270 | 265 | 268 | Pass |
| 200% Modulus, psi | 618 | 512 | 535 | 580 | 576 | 578 | Pass |
| 300% Modulus, psi | 979 | 813 | 852 | 926 | 926 | 924 | Pass |
| | Sample # | | | | | | |
| | 016 | 017 | 018 | 007 | 008 | 009 | |
| Type A durometer, points | 57 | 57 | 57 | 56 | 56 | 56 | Pass |
| Specific gravity | 1.145 | 1.145 | 1.146 | 1.148 | 1.148 | 1.149 | Pass |

TABLE XI

Physical Testing Results from ARDL Liquid Silicone Rubber Composites
Test Specification: Tear Resistance, ASTM D 624-00 (12), DIE C Material
Tear specimens tested at 20 in/min

| | Samples containing no DNA | | | Samples containing DNA | | | Outcome |
|---|---|---|---|---|---|---|---|
| | Sample # | | | | | | |
| | 010 | 011 | 012 | 001 | 002 | 003 | |
| Tear strength, ppi | 92 | 161 | 157 | 96 | 153 | 182 | Pass |

TABLE XII

Sequencing of DNA recovered from Heat Cured LSR Parts post 4 hrs curing

| | DNA 1 of length A | DNA 2 of length B |
|---|---|---|
| % Sequence differences of center-most bases excluding sequence primers before vs. after 4 hours curing LSR | 7% | 0% No difference |

DNA1 (of specified length A): Comparing the sequence alignment before and after LSR heat cure of the center-most bases, excluding sequencing primers sites results in only 7% sequence differences.
DNA 2 (of specified length B): Comparing the sequence alignment, before and after LSR heat cure of the center-most bases, excluding sequencing primer sites results in no sequence differences.

Thus, while there have been described the preferred embodiments of the present invention, those skilled in the art will realize that other embodiments can be made without departing from the spirit of the invention, which includes all such further modifications and changes as come within the true scope of the claims set forth herein.

We claim:

1. A method of authenticating a conductive silicone-metal composite gasket, the method comprising:

mixing a DNA taggant with conductive solid surface metal microspheres under conditions appropriate for the DNA taggant to adhere to the exterior surface of said metal microspheres to form DNA tagged conductive metal microspheres;

mixing the DNA tagged conductive metal microspheres with a quantity of silver-plated copper filled silicone to create DNA tagged silver-plated copper filled silicone;

molding the DNA tagged silver-plated copper filled silicone;

curing the DNA tagged silver-plated copper filled silicone to form a conductive silicone-metal composite gasket comprising said DNA tagged conductive metal microspheres, wherein the physical, conductive and electromagnetic shielding properties of the silicone-metal composite gasket formed from the DNA tagged silver-plated copper filled silicone are identical to said properties of a conductive silicone-metal composite gasket manufactured from non-DNA tagged silver-plated copper filled silicone;

placing a sample of said silicone-metal composite gasket formed from the DNA tagged silver-plated copper filled silicone into a polymerase chain reaction (PCR) vessel thereby performing in situ PCR to amplify the DNA taggant contained within the silicone-metal composite gasket; and detecting the DNA taggant via capillary electrophoresis.

2. The method of claim 1, wherein the DNA tagged silver-plated copper filled silicone is cured at temperatures equal to or greater than about 150° C.

3. The method of claim 1, wherein the DNA tagged silver-plated copper filled silicone is cured by press curing and post curing.

4. The method of claim 1, wherein the ratio of the DNA tagged conductive metal microspheres to the silver-plated copper filled silicone is between about 1:1 to about 10:1.

5. The method of claim 1, wherein the conductive solid surface metal microspheres comprise silver-plated copper.

6. The method according to claim 1, wherein the DNA taggant is mixed with an additive to form a treated DNA taggant, wherein the additive is methylated polyethylene glycol or un-methylated polyethylene glycol.

7. The method according to claim 1, wherein the DNA taggant is mixed with an additive to form a treated DNA taggant, wherein the additive is selected from the group consisting of a polyol, a diol, a glycol, a starch and a pyrrolidone.

* * * * *